US006409726B1

(12) United States Patent
Ellman et al.

(10) Patent No.: US 6,409,726 B1
(45) Date of Patent: Jun. 25, 2002

(54) ELECTROSURGICAL INSTRUMENT FOR EAR SURGERY

(76) Inventors: Alan G. Ellman; Jon C. Garito, both of 1135 Railroad Ave., Hewlett, NY (US) 11557

( * ) Notice: Subject to any disclaimer, the term of this patent is extended or adjusted under 35 U.S.C. 154(b) by 19 days.

(21) Appl. No.: 09/705,201

(22) Filed: Nov. 3, 2000

Related U.S. Application Data

(63) Continuation-in-part of application No. 09/483,993, filed on Jan. 18, 2000, which is a continuation-in-part of application No. 09/435,677, filed on Nov. 8, 1999.

(51) Int. Cl.$^7$ ................................................ A61B 18/18
(52) U.S. Cl. ........................................ 606/45; 606/41
(58) Field of Search .............................. 606/41, 45, 46, 606/47, 48, 49, 50

(56) References Cited

U.S. PATENT DOCUMENTS

| 5,741,250 A | 4/1998 | Garito et al. |
| 6,106,524 A | * 8/2000 | Eggers et al. ................. 606/41 |
| 6,261,241 B1 | * 7/2001 | Burbank et al. ............ 600/564 |

* cited by examiner

*Primary Examiner*—R. Kearney

(57) ABSTRACT

An electrode for use in an electrosurgical aural procedure known as a myringotomy for removing tissue of the tympanic membrane. In a preferred embodiment, the electrode is unipolar and characterized by a a flared tapered conical body terminating in a sharp point, the widest part of the tapered conical body having a diameter of about 1.5-3 mm, being the size of a hole to be formed by vaporization in the tympanic membrane.

6 Claims, 1 Drawing Sheet

ELECTROSURGICAL INSTRUMENT FOR EAR SURGERY

RELATED APPLICATION

U.S. application, Ser. No. 09/435,677, filed Nov. 8, 1999, commonly owned, for "Electrosurgical Instrument for Ear Surgery", of which the present application is a continuation-in-part.

U.S. application, Ser. No. 09/483,993, filed Jan. 18, 2000, commonly owned, for "Electrosurgical Instrument for Ear Surgery", of which the present application is also a continuation-in-part.

This invention relates to an electrosurgical instrument for ear surgery, and in particular, for use in a myringotomy procedure.

BACKGROUND OF THE INVENTION

Reference is made to our prior issued U.S. Pat. No. 5,741,250, whose contents are incorporated herein by reference. This prior patent describes an improved myringotomy surgical procedure involving an incision of the tympanic membrane that is made to allow ventilation of the middle ear, to permit drainage of middle ear fluid, or to obtain cultures from an infected middle ear. The improved procedure uses a solid wire electrode and electrosurgical apparatus to form the hole in the tympanic membrane. The electrosurgical procedure has the important advantage of being able to cut the tissue while at the same time coagulating the cut tissue causing minimum bleeding. The structure of the novel electrode described in the prior patent used to make the incision prevents the excision depth from exceeding a safe value. In accordance with another feature of that invention, the electrode is uniquely configured to enable the active tip to reach the tympanic membrane via the ear canal passageway and incise the desired tissue while avoiding damage to surrounding tissue. The procedure, which has come to be known as radiofrequency assisted tympanostomy (RAT), has so far proven to be safe, cost-effective, and can be performed in an office setting. The opening created by the procedure is reasonably precise, bloodless, and can be carried out in less than one second under topical anesthetic.

Recently, a new treatment called OtoScan Laser Assisted Myringotomy (OtoLAM) has been described. It uses a $CO_2$ laser to vaporize an allegedly precisely-sized preset hole in the tympanic membrane without damaging surrounding structures. The preset hole remains open for several weeks allowing ventilation of the middle ear and avoiding the need for grommets to keep the hole open until the middle ear region is adequately drained. The main disadvantage of this procedure is the use of a highly expensive laser instrument requiring training for those physicians that are not familiar with such equipment.

Our prior filed patent application, Ser. No. 09/435,677, whose contents are incorporated herein by reference, describes an improved electrode for a myringotomy surgical procedure comprising a hollow tube with a sharpened edge or a conically pointed electrode dimensioned to produce a desired hole size.

Our prior filed patent application, Ser. No. 09/483,993, whose contents are incorporated herein by reference, describes an improved electrode for a myringotomy surgical procedure comprising a bare end having a sharp circular edge. In another embodiment, the bare end is solid and has a tapered cone shape. When the electrode end is placed against the tympanic membrane and the electrosurgical apparatus activated, a 2 mm hole is punched in the tympanic membrane which allows any middle ear fluid to drain.

SUMMARY OF THE INVENTION

An object of the invention is a further improved electrosurgical electrode adapted for use in a myringotomy surgical procedure, as well as the myringotomy procedure using the new electrode.

The present invention is a continuation-in-part of the prior pending applications and hereby incorporates by reference the total contents of the prior applications. The present invention describes an additional electrode for use in a myringotomy surgical procedure but otherwise makes use of the same teachings of the prior applications, and for this reason it was felt unnecessary to repeat in the body of this specification the total contents of the prior applications. The present description will be confined solely to the differences in the electrode ends to achieve certain benefits that may be more difficult to achieve with the electrode constructions of the prior application.

The procedure using our novel electrosurgical electrode of the present invention 5 is based on forming a hole in the tympanic membrane, preferably of approximately 1.5–3 mm in size, which is large enough to remain open to allow adequate drainage from the middle ear over several weeks, but not too large so as to delay healing. It is also possible to insert a tube in the hole to maintain it open while it is healing.

In a preferred embodiment, a unipolar electrode is used with a flared conical tip which is supported in an electrically-insulated shaft. The result when applied against the tympanic membrane is to vaporize a hole in the membrane, by the flow of unipolar electrosurgical currents between the flared conical tip and the tissue. This is in contrast with the action of the other myringotomy punch electrodes which act more like a cookie cutter. The main advantage of the invention is that the possibility of the cut tissue disc formed by the myringotomy punch electrode falling behind the tympanic membrane into the ear drum is avoided. The hole formed by vaporization is essentially of the same size as the outer diameter of the electrode tip. Further advantages include better visualization by the surgeon, especially from the side; reproducible ablation or vaporization quality; and a minimal necrosis zone which provides more predictable healing time and scar-free tissue closing.

In comparison with the laser procedure, the electrosurgical equipment is far less expensive and many physicians are already trained in the use of electrosurgical apparatus. Moreover, for those untrained, the training procedure is relatively simple and consumes little time.

As described in the prior patent, the electrode of the invention is also configured to enable the active tip to reach the tympanic membrane via the ear canal passageway and punch the desired tissue hole while avoiding damage to surrounding tissue.

In accordance with the present invention, the incision is effected with the bare flared conical end moved by the surgeon in a generally straight path, and the adjacent portions of the hollow end support and electrode shaft are made insulating to prevent accidental burns to the patient and to allow the physician to use these insulated parts to help position and guide the active tip portion during the surgical procedure. The electrosurgical procedure has the usual advantage of being able to form the tissue hole while at the same time coagulating the tissue edges causing minimum bleeding. It is preferred that the electrosurgical currents used be above 2 MHz, and preferably above 3 MHz. 3.8–4.0 MHz is preferred. At these higher frequencies, commonly referred to as radiosurgery, the hole is formed by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

Figure 1:
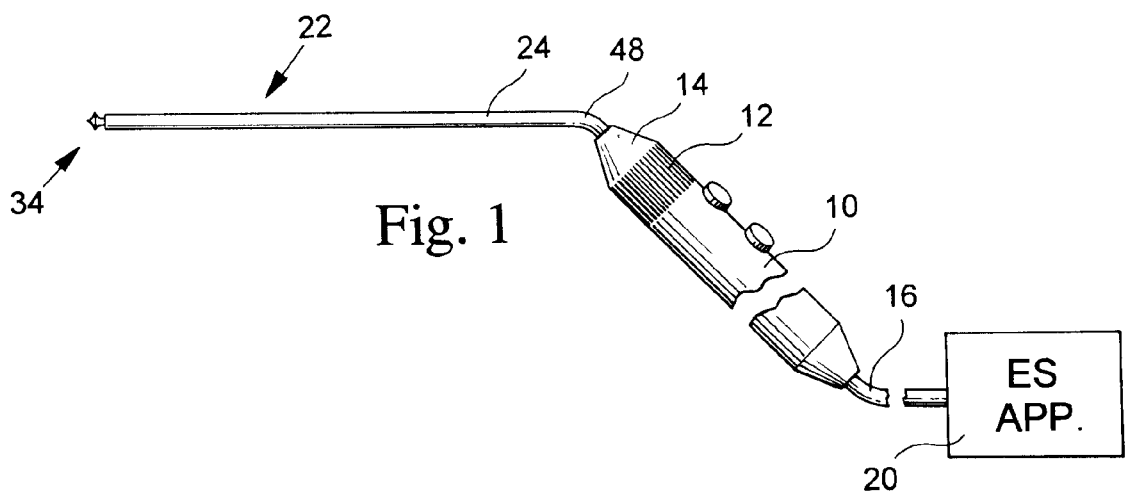
FIG. 1 is a plan view of a unipolar embodiment of an electrosurgical myringotomy or RAT electrode in accordance with the invention, shown mounted in a handpiece which is in turn connected to electrosurgical apparatus.
Figure 2:
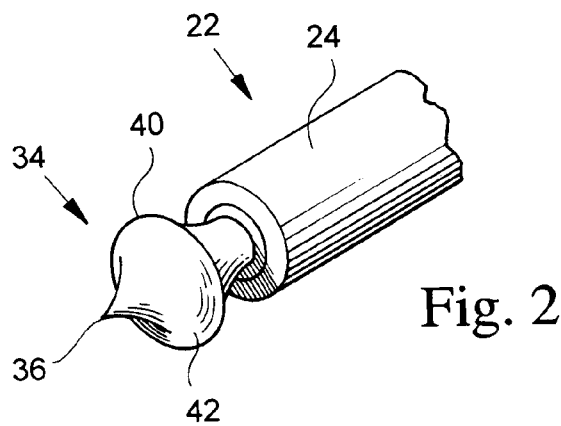
FIG. 2 is a perspective view of the working end of the embodiment of FIG. 1.
Figure 3:
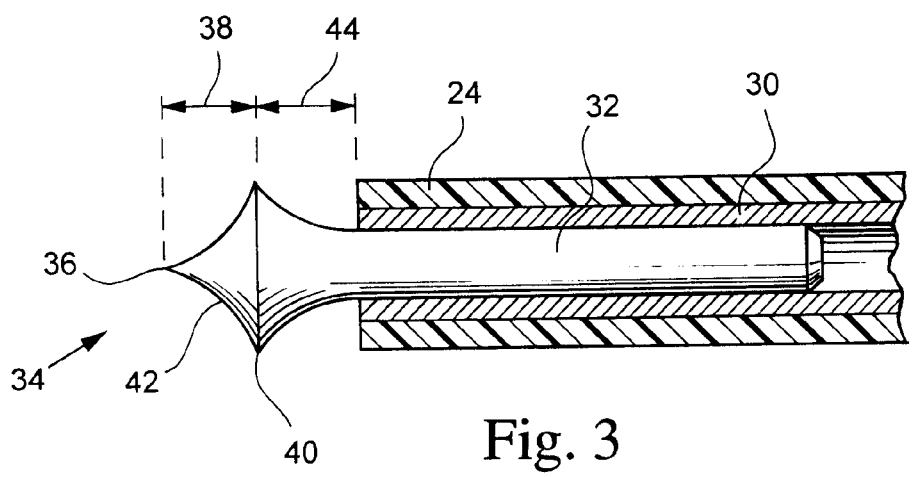
FIG. 3 is a cross-sectional view of the working end of the electrode of FIG. 1.

FIGS. 1–3 illustrate a first preferred form of a unipolar electrosurgical myringotomy electrode of the invention. It comprises a standard electrosurgical handpiece 10 comprising a collet 12, a nosepiece 14, and a cable 16 connected to the handpiece whose other end is connected via a connector to electrosurgical apparatus 20. As an example only, the electrosurgical apparatus 20 can be Model Dual Frequency Surgitron available from Ellman International, Inc. of Hewlett, N.Y. The Ellman equipment is preferred due to its high operating frequency, preferably at 3.8–4.0 MHz.

The electrode 22 itself comprises a bent elongated inner metal tube 30 covered with electrically-insulating material 24, for example, a heat-shrunk plastic tube. In operation, a bare end (not shown) of the tube 23 is mounted through the nosepiece 14 in the collet 12 which is electrically-connected to the cable 16. Mounted as by welding or by a press fit in the distal end of the metal tube 30 via a shank end 32 is a short bare electrically-conductive metal part. The shank end 32 terminates in a bare circular-cylindrical flared conical tip 34 axially aligned with the longitudinal axis (horizontal in FIG. 3). The bare flared conical tip 34 serves as the working end of the electrode. Also connected to the electrosurgical apparatus 20 is the usual indifferent plate (not shown) which during use is in contact with a patient's body. When the electrosurgical apparatus 20 is energized, high frequency electrosurgical currents are generated which are coupled by way of the cable 16 and electrically-conductive tube 30 to the active, bare end 34. The physician, in the usual way, holds the handpiece 10 while applying the active working end 34 of the electrode to the desired area of the patient to be treated. By "flared conical tip" is meant a curving-inward conical surface 42 from a distal central point 36 approximately forming in a plan view a concave taper having a minor arc generated from a radius whose center lies outside of the surface.

In the version depicted in FIG. 1, the bare active end 34 has a sharp point 36 which flares into the concave tapered conical surface 42, for example, about 0.033–0.05 inches long, preferably about 0.039 inches long, which is the dimension indicated by 38, from the point 36 to the periphery of the wide part of the cone, indicated at 40. The outside diameter of the of the wide part of the cone 40 is preferably equal to the tympanic membrane hole diameter desired, preferably about 0.078 inches (2 mm). The concave taper is curved formed by an external radius of about 0.058–0.068 inches long, preferably about 0.063 inches. The space between the wide part of the cone 40 and the adjacent edge of the insulated tube 24, indicated by 44, is about 0.035–0.043 inches long, preferably about 0.039 inches, which limits the length of the active bare end 30 to about 0.08 inches, ensures that the electrode 34 will complete the incision process so long as it is pushed in until the insulated edge of tube 24 is reached. This can be of assistance to the surgeon by coloring the thicker insulating tube 24 differently than that of the bare end 34, so that a clear visual indication is made available to the surgeon. Locating the thicker insulating tube 24 thus about 2 mm from the point 36 allows the facing edge of the thicker tube 24 to act as a stop to limit the penetration to about 2 mm.

The electrically-insulating coating 24 ensures that the only active part of the electrode is the short bare portion 34 in front thereby preventing inadvertant burns or other damage to other ear parts.

The bend 48 in the electrode shaft configures the electrode for easier reaching to the tympanic membrane.

We have invented a novel electrode for use in an electrosurgical myringotomy procedure. This electrosurgical procedure using our novel electrode enables physicians to offer to patients a treatment that is efficiently performed, easily learned and thus performed at a significantly reduced price, and with less tissue damage and bleeding compared to procedures done with other known devices.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A unipolar electrosurgical electrode for forming a hole in the tympanic membrane of a patient, comprising:

a) an electrode holder, b) an electrically-conductive member having a first end and a second end mounted in the holder, c) said second end having an active, electrically-conductive, end portion comprising a tapered flared conical body terminating in a sharp point forming a flared conical tip, the widest part of the tapered conical body having a diameter of about 1.5–3 mm, d) said active end portion being exposed electrically for applying unipolar electrosurgical currents to said tympanic membrane when the electrically-conductive member is connected to a source of electrosurgical currents, e) portions of the electrode holder adjacent said exposed end portion being electrically-insulating to prevent contact and passage of electrosurgical currents to tissue areas adjacent to or surrounding the hole to be formed, f) whereby a 1.5–3 mm hole is formed in the tympanic membrane when the electrosurgical source is activated and the exposed end of the electrode is placed against the tympanic membrane.

2. An electrosurgical electrode as claimed in claim 1, wherein the flared conical body comprises a concave tapered section about 0.033–0.05 inches long terminating in the sharp point.

3. An electrosurgical electrode as claimed in claim 2, wherein the tapered section defines an inwardly-curved conical surface having a radius of curvature of about 0.058–0.068 inches.

4. An electrosurgical electrode as claimed in claim 2, wherein the tapered section from the sharp point to the widest part of the taper is about 0.035–0.043 inches.

5. An electrosurgical electrode as claimed in claim 1, wherein the electrically-insulating portion of the holder is spaced about 2 mm from the sharp point.

6. An electrosurgical electrode as claimed in claim 5, wherein the electrode has a long axis and the tapered section is axially aligned with the long axis.

* * * * *